United States Patent [19]

Merkle et al.

[11] Patent Number: 5,744,614
[45] Date of Patent: Apr. 28, 1998

[54] PREPARATION OF 3,5-DIARYLPYRAZOLES

[75] Inventors: Hans Rupert Merkle, Ludwigshafen; Erich Fretschner, Neckarsteinach, both of Germany

[73] Assignee: BASF Aktiengesellschaft, Ludwigshafen, Germany

[21] Appl. No.: 860,026
[22] PCT Filed: Jan. 4, 1996
[86] PCT No.: PCT/EP96/00011
§ 371 Date: Jul. 3, 1997
§ 102(e) Date: Jul. 3, 1997
[87] PCT Pub. No.: WO96/21650
PCT Pub. Date: Jul. 18, 1996

[30] Foreign Application Priority Data

Jan. 13, 1995 [DE] Germany .............. 195 00 838.3

[51] Int. Cl.⁶ .................................. C07D 231/12
[52] U.S. Cl. ........................................ 548/377.1
[58] Field of Search ............................. 548/377.1

[56] References Cited

U.S. PATENT DOCUMENTS 3,952,010  4/1976  Garber et al. ............... 260/310

Primary Examiner—Johann Richter
Assistant Examiner—Laura L. Stockton
Attorney, Agent, or Firm—Keil & Weinkauf

[57] ABSTRACT

A process for preparing 3,5-diarylpyrazoles of the general formula I

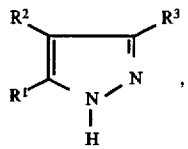

where the substituents have the following meanings:
$R^1$ and $R^3$ are unsubstituted or substituted aryl radicals, $R^2$ is hydrogen, $C_1$–$C_8$-alkyl or unsubstituted or substituted aryl,
in which hydrazine hydrate is reacted with a 1,3-diarylpropenone of the general formula II

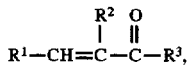

where the substituents $R^1$, $R^2$ and $R^3$ have the abovementioned meanings, in sulfuric acid in the presence of iodine or an iodine compound, is described.

5 Claims, No Drawings

PREPARATION OF 3,5-DIARYLPYRAZOLES

This application is a 371 of PCT/EP96/00011 filed Jan. 4, 1996.

The present invention relates to a novel process for preparing 3,5-diarylpyrazoles of the general formula I

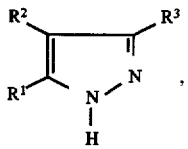

where the substituents have the following meanings:
$R^1$ and $R^3$ are unsubstituted or substituted aryl radicals, $R^2$ is hydrogen, $C_1$–$C_8$-alkyl or unsubstituted or substitued aryl.

3,5-Diphenylpyrazole can be prepared by reaction of diphenylpropane-1,3-dione (dibenzoylmethane) with hydrazine hydrate, which is described, for example, in U.S. Pat. No. 3,882,142.

Furthermore, the reaction of benzylideneacetophenone dibromide with hydrazine hydrate leads to 3,5-diphenylpyrazole (Freudenberg, Stoll, Justus Liebigs Ann. Chem., 440 (1924), 45).

Other possibilities of preparation are dehydrogenations of 3,5-diphenylpyrazolines by, for example, catalytic dehydrogenation according to U.S. Pat. No. 4,014,896, U.S. Pat. No. 3,952,010 and DE 24 41 504.

The appropriate pyrazolines can be obtained by reacting chalcones (1,3-diarylpropenones, eg. benzylideneacetophenone) with hydrazine hydrate in alcoholic solution (Kishner Zh. Russ. Fiz.-Khim. O-va 47 (1915) 1102; Centralblatt, 1916 I, 1063).

A further possibility of synthesis of 3,5-diphenylpyrazoline is the reaction of phenylphenylacetyle-nylcarbinol with hyrazine hydrate (Stoll, Justus Liebigs Ann. Chem., 440 (1924), 39, 42).

In addition to the preparation of pyrazoles by dehydrogenation of 3,5-disubstitued pyrazolines, U.S. Pat. No. 4,014,896, U.S. Pat. No. 3,952,010 and DE 24 41 504 also describe the synthesis of the latter by reaction of 1,3-disubstituted propenones with hydrazine hydrate. The procedure used here is in general one in which a methyl aryl ketone, eg. acetophenone, is reacted with benzaldehyde in methanol in the presence of bases to give the corresponding 1,3-disubstituted propenones which, after acidifying with mineral acids, react with hydrazine hydrate to give the desired pyrazolines.

EP 402 722 discloses a further process for preparing pyrazole by dehydrogenation of 2-pyrazoline.

Since the pyrazole syntheses described are multistage syntheses, the object was therefore to make 3,5-diarylpyrazoles accessible in a technically simpler and more economical manner.

Accordingly, a process has been found for preparing 3,5-diarylpyrazoles of the general formula I

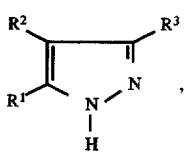

where the substituents have the following meanings:
$R^1$ and $R^3$ are unsubstituted or substituted aryl radicals, $R^2$ is hydrogen, $C_1$–$C_8$-alkyl or unsubstituted or substituted aryl, in which hydrazine hydrate is reacted with a 1,3-diarylpropenone of the general formula II

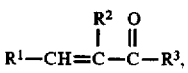

$$R^1-CH=C-C-R^3,$$
with $R^2$ above O above (double bond)

where the substituents $R^1$, $R^2$ and $R^3$ have the abovementioned meanings, in sulfuric acid in the presence of iodine or an iodine compound.

It has furthermore been found that instead of 1,3-diarylpropenones of the general formula II, their starting compounds, a carbonyl compound of the general formula III

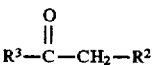

$$R^3-C-CH_2-R^2$$

and an arylaldehyde of the general formula IV $$R^1-CHO \qquad \text{IV,}$$

where the substituents $R^1$, $R^2$ and $R^3$ have the abovementioned meanings, can be used.

The reaction proceeds in a one-pot process.

The 1,3-disubstituted pyrazoline formed from hydrazine hydrate and the appropriate 1,3-diarylpropenone of the formula II or its starting substances, the carbonyl compound of the formula III and arylaldehyde of the formula IV, is dehydrogenated in the reaction mixture to the corresponding 3,5-diarylpyrazole by the iodine formed from hydrogen iodide and sulfuric acid, corresponding amounts of sulfur dioxide being liberated by the oxidation of hydrogen iodide to iodine by sulfuric acid. The reactants hydrazine hydrate and 1,3-diarylpropenone of the formula II or their starting substances, the carbonyl compound of the formula III and arylaldehyde of the formula IV, are reacted in stoichiometric amounts, it being possible to employ the reactants in an excess or insufficient amount.

The sulfuric acid, which is employed as an oxidant and also as a diluent, is in general employed in a from 0.5- to 10-fold excess, where the sulfuric acid should be present in a concentration of not less than 30% by weight, preferably of from 45 to 95% by weight.

Iodine or the iodine compound is in general employed in the reaction in amounts of from 0.01 to 10 mol % per mole of the hydrazine employed, preferably from 0.05 to 5 mol % and in particular from 0.1 to 2 mol %.

In addition to elemental iodine, iodine compounds such as hydrogen iodide, alkali metal and alkaline earth metal iodides such as lithium iodide, sodium iodide, potassium iodide, cesium iodide, magnesium iodide and calcium iodide and also other metal iodides are suitable; other inorganic iodine compounds such as alkaline earth metal and alkali metal hypoiodides, iodites, iodates and periodates or organic iodine compounds such as alkali metal iodides, eg. methyl iodide, can also be used.

This one-pot reaction is in general carried out at normal pressure at from 50° C. to 250° C., preferably at from 70° C. to 200° C., in particular at from 90° C. to 170° C. The reaction can also be carried out at elevated pressure and also under reduced pressure. The reaction can also be carried out stepwise such that the formation of 1,3-diarylpropenone is first carried out at from 20° C. to 100° C. in sulfuric acid, it being possible for the amount of sulfuric acid needed for complete reaction to be initially introduced completely or partly. The reaction mixture is then reacted with hydrazine hydrate in the presence of iodine and possibly of additional sulfuric acid at from 50° C. to 150° C., preferably at from 70° C. to 200° C., in particular at from 90° C. to 170° C.

The reaction is in general carried out such that all the reaction components are combined in the reaction vessel and then jointly heated to the reaction temperature. However, the reactants, apart from sulfuric acid, can also be introduced separately or as a mixture into preheated sulfuric acid/NaI solution or some of the reactants can be initially introduced at the reaction temperature and the other reactants added at a higher temperature. The water of reaction is distilled off during the reaction.

The diarylpyrazole formed precipitates even at reaction temperature and can be completely crystallized by cooling. The material from the reaction can be neutralized by addition of dilute sodium hydroxide solution. The neutralization of the sulfuric acid present in the reaction mixture can be dispensed with, however, because the 3,5-diarylpyrazoles do not form any salts with sulfuric acid under these conditions. The reaction suspension therefore can also be diluted by addition of water alone and filtered. The diarylpyrazoles are obtained in high yield and purity.

The process according to the invention is suitable for preparing 3,5-diarylpyrazoles of the general formula I

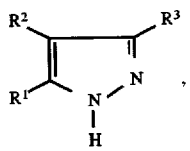

where the substituents have the following meanings:

$R^1$ and $R^3$ are unsubstituted or substituted aryl radicals, $R^2$ is hydrogen, $C_1$–$C_8$-alkyl or unsubstituted or substituted aryl.

Unsubstituted or substituted aryl includes phenyl and substituted phenyl. Suitable substituted phenyl includes phenyl substituted by $C_1$–$C_8$-alkyl, $C_1$–$C_8$-alkoxy, halogen, nitro, sulfonic acid, $C_3$–$C_8$-cycloalkyl or allyl.

With respect to the novel process, it is particularly preferred to carry out the reaction in the form of a one-pot reaction without isolating one of the intermediates. In this case the reaction is expediently carried out in such a way that 1,3-diarylpropenones of the formula II or the carbonyl compounds of the formula III and arylaldehydes of the formula IV are simultaneously reacted, separately or as a mixture, with the stoichiometric amount of hydrazine hydrate or with an excess or insufficient amount of hyrazine hydrate under the conditions outlined above in sulfuric acid in the presence of iodine or an iodine compound.

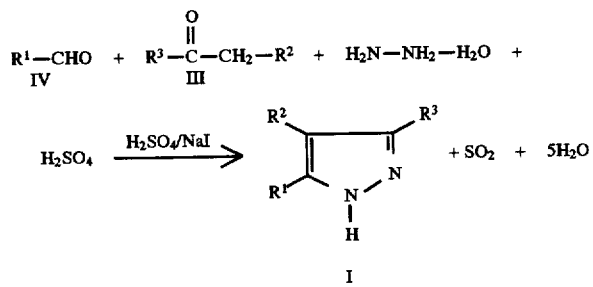

In the process according to the invention, it is of little importance for yield and purity in which sequence the reactants are added, ie. the carbonyl compound of the formula III and arylaldehyde of the formula IV can be initially introduced in sulfuric acid, the corresponding 1,3-diarylpropenones of the formula II being formed, and hydrazine hydrate added.

Likewise, hydrazine hydrate can be initially introduced into sulfuric acid and the diarylpropenone of the formula II or a mixture of its starting substances, the carbonyl compound of the formula III and arylaldehyde of the formula IV, added. In just the same way, 1,3-diarylpropenones or mixtures of carbonyl compounds of the formula III and arylaldehydes of the formula IV and hydrazine hydrate can be introduced separately, simultaneously or in succession into the sulfuric acid brought to reaction temperature, which is treated with NaI, and reacted. The iodine or iodine compound catalyst can be initially introduced or added during the reaction.

Under the reaction conditions, the intermediates are probably generated in situ and react to give the compounds according to the invention according to the following scheme.

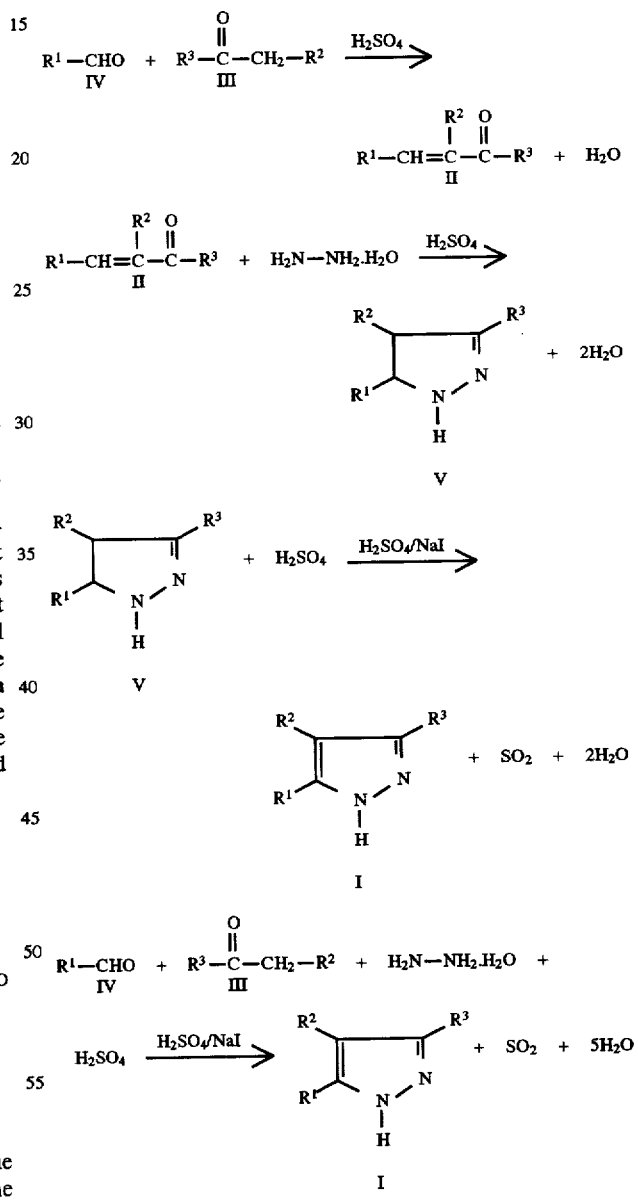

EXPERIMENTAL EXAMPLES

Example 1

60 parts (0.5 mol) of acetophenone and 53 parts (0.5 mol) of benzaldehyde were simultaneously added dropwise at 40° C. to 326.7 parts (2.0 mol) of 60% strength by weight sulfuric acid in the course of 30 minutes. The mixture was stirred at 40° C. for 30 minutes and the phases were then separated. The sulfuric acid phase was initially introduced into a four-necked flask with 0.5 parts (0.0033 mol) of sodium iodide and heated to 130° C. The upper phase was then simultaneously added dropwise with 25 parts (0.5 mol) of hydrazine hydrate in the course of 30 minutes. The temperature fell from 130° C. to 120° C. during the addition. The temperature was again brought to 130° C. by distilling off water and kept at 130° C. for 2 hours by further distillation of water. The amount of water distilled off was 70 ml. The mixture was diluted at 100° C. with 250 ml of water and neutralized at 70° C. with 497 parts (3.1 mol) of 25% strength sodium hydroxide solution. The precipitate was filtered off with suction at 25° C. and washed with water until sulfate-free. After drying, 105.5 parts of 3,5-diphenylpyrazole were obtained having a purity of 98.5% (HPLC), which corresponds to a yield of 94.4% of theory. M.p.: 199° C.

Example 2

120 parts (1 mol) of acetophenone and 106 parts (1 mol) of benzaldehyde were simultaneously added dropwise at 70° C. to 490 parts (3 mol) of 60% strength by weight sulfuric acid. The mixture was stirred at 70° C. for 2 hours and the phases were then separated. The sulfuric acid phase was initially introduced with 2 parts (0.0133 mol) of sodium iodide and 62.5 parts (1 mol) of 80% strength by weight hydrazine hydrate were added dropwise. The reaction mixture was heated to reflux (116° C.) and the organic phase was added dropwise in the course of 60 minutes. In order to keep the temperature at 116° C., water was distilled off. The mixture was stirred at 116° C. for 5 hours, 150 ml of water being distilled off in this process. The mixture was diluted with 500 ml of water, and the precipitate was filtered off at room temperature and washed with water until neutral. After drying, 213.3 parts of 3,5-diphenylpyrazole having a purity of 96% (HPLC) were obtained, which corresponds to a yield of 93.1% of theory. M.p.: 196° C.

Example 3

392 parts (2 mol) of 50% strength sulfuric acid and 1 part (0.0067 mol) of sodium iodide were initially introduced into the stirring flask. 60 parts (0.5 mol) of acetophenone, 53 parts (0.5 mol) of benzaldehyde and 25 parts (0.5 mol) of hydrazine hydrate were simultaneously added dropwise under reflux at 124° C. in the course of 30 minutes. The temperature fell to 112° C. By distilling off water, the temperature was brought to 130° C. and the mixture was stirred at 130° C. for 60 minutes. 120 ml of water were distilled off. The reaction mixture obtained was diluted with 250 ml of water and neutralized with 525 parts (3.28 mol) of 25% strength by weight sodium hydroxide solution and filtered. The filter residue was washed with water until sulfate-free and dried. 110.2 parts of 3,5-diphenylpyrazole having a purity of 94.1% (HPLC) were obtained, which corresponds to a yield of 94.3% of theory. M.p.: 194° C.

Example 4

25 parts (0.5 mol) of hydrazine hydrate and 60 parts (0.5 mol) of acetophenone were simultaneously added dropwise to 326.7 parts of initially introduced 60% strength by weight sulfuric acid. The mixture was stirred at 120° C. for 2 hours and then cooled to 50° C. 53 parts (0.5 mol) of benzaldehyde were added dropwise to the reaction mixture and it was stirred at 120° C. for a further 2 hours. 5 parts (0.033 mol) of 10% strength by weight sodium iodide were added dropwise in the course of 10 minutes and the mixture was stirred under reflux for 4.5 hours. After cooling and diluting with 100 parts of water, the reaction product was filtered off and washed with water until neutral. 111.2 parts of 3,5-diphenylpyrazole having a purity of 92.7% (HPLC) were obtained, which corresponds to a yield of 93.7% of theory. M.p.: 192° C.

Example 5

120 parts (1 mol) of acetophenone and 106 parts (0.5 mol) of benzaldehyde were simultaneously added dropwise at 25° C. to 980 parts (6 mol) of initially introduced 60% strength by weight sulfuric acid. The mixture was stirred at 25° C. for 30 minutes and the phases were then separated. The sulfuric acid phase was initially introduced with 2 parts (0.013 mol) of sodium iodide and the organic phase was simultaneously metered in in the course of 10 minutes with 62.5 parts (1 mol) of 80% strength by weight hydrazine hydrate. The mixture was stirred under reflux for 4.5 hours, during the course of which the temperature fell from 123° C. to 119° C. After diluting with 500 parts of water, the mixture was cooled to room temperature and the solid was filtered off. The filter residue was washed with water until neutral and dried. 210.4 parts of 3,5-diphenylpyrazole having a purity of 97.5% (HPLC) were obtained, which corresponds to a yield of 93.2% of theory. M.p.: 198° C.

Example 6

60 parts (0.5 mol) of acetophenone and 53 parts (0.5 mol) of benzaldehyde were simultaneously added dropwise at 25° C. to 140 parts (1 mol) of initially introduced 70% strength by weight sulfuric acid. The mixture was stirred at 25° C. for 60 minutes and the reaction solution obtained was simultaneously added dropwise with 25 parts (0.5 mol) of hydrazine hydrate at 135° C. to 140 parts (1 mol) of initially introduced 70% strength by weight sulfuric acid and 0.5 parts (0.0033 mol) of sodium iodide in the course of 25 minutes. The mixture was stirred at 125° C. for 60 minutes. In order to keep the temperature at 135° C., 38 parts of water were distilled off. The mixture was diluted with 500 parts of water and neutralized with 247.8 parts (3.1 mol) of 50% strength by weight sodium hydroxide solution. After filtering off the solid it was washed until sulfate-free and dried. 109.7 parts of 3,5-diphenylpyrazole having a purity of 96.8% (HPLC) were obtained, which corresponds to a yield of 96.5% of theory. M.p.: 197° C.

Example 7

490 parts (3 mol) of 60% strength by weight sulfuric acid and 1.5 parts (0.01 mol) of sodium iodide were initially introduced into the stirring flask. 46.9 parts (0.75 mol) of 80% strength by weight hydrazine hydrate, 90 parts (0.75 mol) of acetophenone and 79.5 parts (0.75 mol) of benzaldehyde were simultaneously added dropwise at 120° C. in the course of 2 hours. By distilling off 120 parts of water the temperature was kept at 120° C. for 2 hours. The reaction mixture obtained was diluted with the distilled-off water and neutralized with 936 parts (4.7 mol) of 20% strength by weight sodium hydroxide solution. The precipitate was filtered off at room temperature, and the filter residue was washed with water and dried. 162.7 parts of 3,5-diphenylpyrazole having a purity of 96.1% (HPLC) were obtained, which corresponds to a yield of 94.8% of theory. M.p.: 196° C.

Example 8

490 parts (3 mol) of 60% strength by weight sulfuric acid were initially introduced into the stirring flask. 46.9 parts (0.75 mol) of 80% strength by weight hydrazine hydrate, 90 parts (0.75 mol) of acetophenone, 79.5 parts (0.75 mol) of benzladehyde and 1.5 parts (0.01 mol) of sodium iodide were metered in in succession at room temperature. The reaction mixture was brought to 120° C. by distilling off water and kept at 120° C. for 2.5 hours. 110 parts of water were distilled off. The mixture was diluted with the distilled-off water and neutralized with 717 parts (4.5 mol) of 25% strength by weight sodium hydroxide solution. The precipitate was filtered off at room temperature, and the filter residue was washed with water and dried. 160.6 parts of 3,5-diphenylpyrazole having a purity of 94.4% (HPLC) were obtained, which corresponds to a yield of 91.9% of theory. M.p.: 194° C.

Example 9

67.2 parts (0.5 mol) of 4-methylacetophenone and 53 parts (0.5 mol) of benzaldehyde were simultaneously added dropwise at 40° C. to 326.7 parts (2 mol) of 60% strength by weight sulfuric acid. The mixture was stirred at 40° C. for 2 hours and the phases were then separated. The sulfuric acid phase was initially introduced into the reaction flask with 0.5 part (0.0033 mol) of sodium iodide and the organic phase was simultaneously added dropwise at 100° C. in the course of 30 minutes with 25 parts (0.5 mol) of hydrazine hydrate. The mixture was stirred under reflux (114° C.) for 4 hours and then diluted with 250 parts of water. The mixture was neutralized with 477 parts (2.98 mol) of 25% strength by weight sodium hydroxide solution and filtered at room temperature. The filter residue was washed with water and dried. 111.2 parts of 3-phenyl-5-(4-methylphenyl)pyrazole having a purity of 94.7% (HPLC) were obtained, which corresponds to a yield of 90% of theory. M.p.: 175° C.

Example 10

326.7 parts (2 mol) of sulfuric acid were initially introduced into the stirring flask. 37.5 parts (0.75 mol) of hydrazine hydrate, 100 parts (0.75 mol) of 4-methylacetophenone, 105 parts (0.75 mol) of 4-chlorobenzaldehyde and 1 part (0.0067 mol) of sodium iodide were metered in in succession at room temperature. The reaction mixture was brought to 140° C. by distilling off water and kept at 140° C. for 2.5 hours. 140 parts of water were distilled off. The mixture was diluted with 500 parts of water and neutralized with 500 parts (12.5 mol) of 20% strength by weight sodium hydroxide solution. After filtering off the solid it was washed until sulfate-free and dried. 189 parts of 3-(4-chlorophenyl)-5-(4-methylphenyl) pyrazole having a purity of 98% (HPLC) were obtained, which corresponds to a yield of 92% of theory. M.p.: 228° C.

We claim:

1. A process for preparing 3,5-diarylpyrazoles of the general formula I

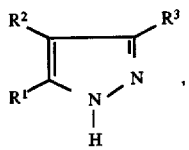

where the substituents have the following meanings:

$R^1$ and $R^3$ are unsubstituted or substituted aryl radicals, $R^2$ is hydrogen, $C_1$–$C_8$-alkyl or unsubstituted or substituted aryl, which comprises reacting hydrazine hydrate with a carbonyl compound of the general formula III

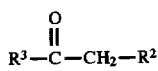

and an arylaldehyde of the general formula IV

where the substituents $R^1$, $R^2$ and $R^3$ have the abovementioned meanings, in sulfuric acid in the presence of iodine or an iodine compound.

2. A process as claimed in claim 1, wherein $R^1$ and $R^3$ are phenyl or phenyl substituted by $C_1$–$C_8$-alkyl, $C_1$–$C_8$-alkoxy, halogen, nitro, sulfonic acid, $C_3$–$C_8$-cycloalkyl or allyl and $R^2$ is hydrogen, $C_1$–$C_8$-alkyl, phenyl or phenyl substituted by $C_1$–$C_8$-alkyl, $C_1$–$C_8$-alkoxy, halogen, nitro, sulfonic acid, $C_3$–$C_8$-cycloalkyl or allyl.

3. A process as claimed in claim 1, wherein the reaction is carried out at from 50° to 250° C.

4. A process as claimed in claim 1, wherein the reaction is carried out in the presence of from 0.01 to 10 mol % of iodine or an iodine compound, based on the hydrazine employed.

5. A process as claimed in claim 1, wherein the reaction is carried out in a from 0.5- to 10-fold excess of sulfuric acid, based on the starting components of the formula II or of the formulae III and IV.

* * * * *